US006756517B2

(12) United States Patent
Kishimoto et al.

(10) Patent No.: US 6,756,517 B2
(45) Date of Patent: Jun. 29, 2004

(54) LOWER ALKANE OXIDATIVE DEHYDROGENATION CATALYSTS AND A PROCESS FOR PRODUCING OLEFINS

(75) Inventors: Nobuji Kishimoto, Himeji (JP); Etsushige Matsunami, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 308 days.

(21) Appl. No.: 09/895,416

(22) Filed: Jul. 2, 2001

(65) Prior Publication Data

US 2001/0049461 A1 Dec. 6, 2001

Related U.S. Application Data

(62) Division of application No. 09/313,652, filed on May 18, 1999, now abandoned.

(30) Foreign Application Priority Data

May 18, 1998 (JP) ............................................. 10-135420

(51) Int. Cl.$^7$ .............................................. C07C 5/333
(52) U.S. Cl. ....................... 585/658; 585/661; 585/662; 585/663; 585/660
(58) Field of Search ................................ 585/658, 661, 585/662, 663, 660

(56) References Cited

U.S. PATENT DOCUMENTS

| | | |
|---|---|---|
| 3,607,966 A | 9/1971 | Croce et al. |
| 3,666,687 A | 5/1972 | Croce et al. |
| 3,873,628 A | 3/1975 | Van Sorge |
| 3,914,389 A | 10/1975 | Haacke |
| 3,925,498 A | 12/1975 | Stadig |
| 3,929,681 A | 12/1975 | Buonomo et al. |
| 3,937,746 A * | 2/1976 | Croce et al. ............... 585/442 |
| 3,997,440 A | 12/1976 | Box, Jr. et al. |
| 4,078,004 A | 3/1978 | Schlaefer et al. |
| 4,107,272 A | 8/1978 | Mori et al. |
| 4,131,631 A | 12/1978 | Hardman |
| 4,330,429 A | 5/1982 | Sasaki et al. |
| 4,370,259 A * | 1/1983 | Eastman et al. ............ 502/208 |
| 4,397,771 A | 8/1983 | Grasselli et al. |
| 4,500,505 A | 2/1985 | Jevnikar et al. |
| 4,777,319 A | 10/1988 | Kung et al. |
| 4,780,445 A | 10/1988 | Jung |
| 4,912,081 A | 3/1990 | Sofranko et al. |
| 4,960,921 A | 10/1990 | Suresh et al. |
| 4,968,656 A | 11/1990 | Fukuda et al. |
| 4,973,397 A | 11/1990 | Ho |
| 5,605,773 A | 2/1997 | Ellgen |
| 5,637,545 A | 6/1997 | Lewis |
| 5,849,257 A | 12/1998 | Fujiwara et al. |

FOREIGN PATENT DOCUMENTS

| | | |
|---|---|---|
| CN | 1073893 A | 10/1992 |
| EP | 379433 A1 | 7/1990 |
| EP | 0557790 | 9/1993 |
| WO | 9736849 | 10/1997 |

OTHER PUBLICATIONS

Neftekhimiya (1990), 30(2) 207–10, and its English abstract.
J. Chem. Commun. (1991) (8) 558–9.
Catal. Lett. (1996), 37, (3,4), 241–6.
ACS Symp. Ser. (1996), 638 (Heterogeneous Hydrocarbon Oxidation) 155–169.
Japanese Laid–Open (KOKAI) Pat. Appln. No. 245494/1996 and English abstract.
Japanese KOKAI No. 045643/1998 and English abstract.
Japanese KOKAI No. 118491/1998 and English abstract.
Japanese KOKAI No. 62041/1980 and U.S. patent No. 4,260,822.
Japanese KOKAI No. 128247/1992 and English abstract.
Patent Abstract of Japan, vol. 016, No. 128, Apr. 2, 1992 & JP 03 293034 A (Sakai Chem Ind Co Ltd).
Database WPI, Section Ch, Week 199430, Derwent Publication Ltd., London, GB; AN 1994–247719.
Database WPI, Section Ch, Week 198903, Derwent Publications Ltd., London, GB; AN 1989–022697.

\* cited by examiner

*Primary Examiner*—Thuan D Dang
(74) *Attorney, Agent, or Firm*—Sherman & Shalloway

(57) ABSTRACT

Lower alkenes of from 2 to 5 carbon atoms, such as propene, are produced by the vapor phase catalytic oxidative dehydrogenation of lower alkane, such as propane, using a mixed metal oxide catalyst of formula (1) as decribed, containing manganese and at least one additional metal as essential elements, e.g., $Mn_1Sb_{0.15}O_x$, $Mn_1P_{0.2}O_x$, $Mn_1S_{0.15}W_{0.05}Cr_{0.1}O_x$. The lower alkene may be further oxidatively dehydrogenated using a mixed metal oxide catalyst of formula (1), especially formula (2), as described, to produce a mixture of unsaturated aldehyde and unsaturated acid. The unsaturated aldehyde may be further oxidatively dehydrogenated in the vapor phase in the presence of mixed metal oxide catalyst of formula (1), especially formula (3).

6 Claims, No Drawings

LOWER ALKANE OXIDATIVE DEHYDROGENATION CATALYSTS AND A PROCESS FOR PRODUCING OLEFINS

CROSS-REFERENCE TO RELATED APPLICATIONS

This application is a division of application Ser. No. 09/313,652, filed May 18, 1999 now abandoned.

TECHNICAL FIELD TO WHICH THE INVENTION BELONGS

This invention relates to lower alkane oxidative dehydrogenation catalysts and a production process of olefins using said catalysts. More specifically, the invention relates to the catalysts which are suitable for use in vapor phase oxidative dehydrogenation of $C_2$–$C_5$ lower alkanes (hereinafter occasionally referred to simply as "lower alkanes") in the presence of molecular oxygen to produce corresponding olefins, and a process for oxidizing and dehydrogenating lower alkanes with molecular oxygen to produce corresponding olefins at high yields, with the use of said catalysts.

The invention also relates to a process for producing, from the olefins which have been obtained through vapor phase oxidative dehydrogenation of $C_2$–$C_5$ lower alkanes in the presence of molecular oxygen, the corresponding unsaturated aldehydes and/or unsaturated carboxylic acids.

PRIOR ART

As a production process for lower olefins, in particular, propylene and isobutene, simple dehydrogenation process of lower alkanes is recently reduced to industrial practice. However, this process is subject to an essential problem that it is incapable of giving high conversion due to the equilibrium limitation and furthermore requires high temperatures. Still in addition, deterioration of the catalyst within a short period is inavoidable in said process, which necessitates frequent regeneration of the catalyst using a switch converter or the like. In consequence, plant construction costs and utility costs for running the process are high and, depending on the conditions of location, it is unprofitable and its industrial application is restricted.

Whereas, attempts to produce lower olefins from lower alkanes through oxidative dehydrogenation which is free from the limitation by equlibrium have been made since long, and various catalyst systems therefor have been proposed. Among those known, there are Co—Mo oxide catalyst (U.S. Pat. No. 4,131,631), V—Mg oxide catalyst (U.S. Pat. No. 4,777,319), Ni—Mo oxide catalyst (EP 379,433 A1) $CeO_2/CeF_3$ catalyst (CN 1,073,893A), Mg—Mo catalyst [Neftekhimiya (1990), 30(2) 207–10], $V_2O_5/Nb_2O_5$ catalyst [*J. Chem. Commun.* (1991) (8) 558–9], rare earth vanadates catalyst [*Catal. Lett.* (1996), 37, (3, 4), 241–6] and $B_2O_3/Al_2O_3$ catalyst [*ACS Symp. Ser.* (1996), 638 (Heterogeneous Hydrocarbon Oxidation) 155–169). Those known catalysts, however, invariably show very low level oxidative dehydrogenation performance, the property of the prime importance, and are far short of industrial practice.

Japanese Laid-open (KOKAI) Patent Application, KOKAI No. 245494/1996 furthermore contains a disclosure on a process for further oxidizing propylene, which was formed through dehydrogenation of propane, to produce acrylic acid. This process, however, necessitates removal of the hydrogen formed during the dehydrogenation of propane from the reaction gas. Japanese KOKAI Nos. 045643/1998, 118491/1998, 62041/1980 and 128247/1992, etc. disclose processes for forming unsaturated aldehydes and/or acids from lower alkanes, in particular, acrolein and/or acrylic acid from propane and methacrolein and/or methacrylic acid from isobutane. However, yield of these object products indicated in these publications are very low, and the processes need to be improved in various aspects including the catalyst to be used.

THE PROBLEM TO BE SOLVED BY THE INVENTION

An object of this invention is to provide novel oxidative dehydrogenation catalysts useful for vapor phase oxidative dehydrogenation of lower alkanes with molecular oxygen to produce corresponding lower olefins at high yield; and also to provide a process for producing from lower alkanes the corresponding olefins at high yield, by the use of said catalysts.

Another object of the invention is to provide a process for producing from lower alkanes corresponding unsaturated aldehydes and/or unsaturated carboxylic acids at high yield.

MEANS FOR SOLVING THE PROBLEM

We have made concentrative studies in search of the catalysts suitable for oxidizing and dehydrogenating lower alkanes with molecular oxygen to produce the corresponding lower olefins, to discover that a catalyst containing manganese as the indispensable component, or a catalyst in which said catalytically active component is supported on a refractory inorganic carrier exhibit excellent oxidative dehydrogenation performance; and that lower olefins could be produced at high yield with the use of said catalyst. The present invention has been completed based on these discoveries.

Thus, the present invention provides catalysts for oxidative dehydrogenation of lower alkanes, said catalysts being suitable for use in vapor phase oxidative dehydrogenation of $C_2$–$C_5$ lower alkanes in the presence of molecular oxygen to produce corresponding olefins and characterized by having a composition expressed by a general formula (I) below:

$$Mn_\alpha E^1_\beta E^2_\gamma Ox \quad (1)$$

(in which Mn denotes manganese, and O, oxygen; $E^1$ is at least one element selected from the group consisting of P, As, Sb, B, S, Se, Te, F, Cl, Br, I, Nb, Ta, W, Re and Cu; $E^2$ is at least one element selected from the group consisting of Cr, Fe, Co, Ni, Ag, Au, Zn, Tl, Sn, Pb, Bi, Li, Na, K, Rb, Cs, Mg, Ca, Sr, Ba, Y, La, Ce, Nd and Sm; and $\alpha$, $\beta$, $\gamma$ and x denote atomic numbers of Mn, $E^1$, $E^2$ and oxygen, respectively, where when $\alpha$=1, $\beta$=0.01–10, $\gamma$=0–5, and x is a numerical value determined by the state of oxidation of those elements other than oxygen).

The present invention furthermore provides a process for producing olefins which comprises vapor phase oxidative dehydrogenation of $C_2$–$C_5$ alkanes in the presence of molecular oxygen to form corresponding olefins, characterized by the use of the above-described catalyst.

According to the present invention, furthermore, a process for producing, from lower alkane, unsaturated aldehyde and unsaturated acid at high yield is provided, in which an olefin obtained through vapor-phase oxidative dehydrogenation of $C_2$–$C_5$ lower alkanes in the presence of molecular oxygen using the above-defined catalyst is further oxidized at vapor phase in the presence of oxygen to provide unsaturated aldehyde and unsaturated acid.

The invention moreover provides a process for producing unsaturated acid from lower alkane at high yield, in which the unsaturated aldehyde obtained as above is further oxidized at vapor phase in the presence of molecular oxygen to provide unsaturated acid.

EMBODIMENTS OF THE INVENTION

More specifically, $C_2$–$C_5$ lower alkanes signify ethane, propane, n-butane, isobutane, n-pentane and isopentane. The catalysts of the present invention are used in oxidative dehydrogenation reactions of these lower alkanes to produce corresponding olefins, more specifically, ethylene from ethane, propylene from propane, n-butene from n-butane, isobutene from isobutane, n-pentene from n-pentane and isopentene from isopentane. These lower alkanes may be used either singly or as a mixture of more than one. The oxidative dehydrogenation catalysts of the present invention are useful for the production of, in particular, propylene and isobutene from propane and isobutane, respectively.

Referring to the general formula (I), the catalysts in which, when $\alpha=1$, $\beta=0.02$–2, and $\gamma=0$–1 are particularly preferred.

For improving the selectivity for, and yield of, the product, the catalysts of the general formula (I) in which $E^1$ component is P, Sb, B, S, Nb, W or Re and $E^2$ component is Cr, Fe, Sn, Na, Mg or Ce are preferred.

The oxidative dehydrogenation catalysts of general formula (I) of the present invention may be used as supported on a refractory inorganic carrier for the purpose of improving activity level and physical durability. As the refractory inorganic carrier, those generally used in preparation of this type of catalysts can be used, the representative examples thereof including silica, alumina, titania, zirconia, silica-alumina, silica-titania and silica-zirconia. In particular, silica and silica-alumina are preferred, because they give higher yield of object products. The ratio of silica in the silica-alumina catalyst system normally ranges from 10% by weight to less than 100% by weight. The amount of the catalytically active component to be carried is normally between 10 and 90% by weight of the refractory inorganic carrier.

The method of preparation of the oxidative dehydrogenation catalysts of the present invention is not subject to any critical limitations, but any of conventionally practiced methods or known methods for preparation of this type of catalysts can be used. For example, the catalysts may be prepared by the procedures comprising adding to a slurry of manganese dioxide powder antimony trioxide powder and aqueous solutions of phosphoric acid, boric acid, ammonium sulfate, telluric acid, ammonium chloride, niobium oxalate, ammonium tungstate, rhenium oxide and copper nitrate, etc. as $E^1$ component; if necessary further adding aqueous solution of at least one element selected from the $E^2$ component; further if necessary adding a carrier such as silica, alumina or the like thereto; condensing the mixture under heating with agitation for a prescribed period, drying the resultant paste at 80–300° C.; pulverizing and molding the same; if necessary further crushing the same for size adjustment or re-drying at 80–300° C.; and if necessary further firing the dry product at 300–800° C. The firing atmosphere is subject to no limitation, and the firing may be conducted in air, an atmosphere of high or low oxygen concentration, a reducing atmosphere, in an inert gas such as nitrogen, helium, argon or the like, or in vacuum. In most desirable practice, the catalyst is not fired at the high temperatures but is contacted with the reaction gas containing the alkane or alkanes and oxygen as it has undergone the drying treatment or treatments at not higher than 300° C. In that occasion, the reaction may be started at a temperature not lower than the prescribed level by way of a pretreating reaction, or directly at the prescribed temperature. In the latter case changes in catalytic activity may be observed at the initial stage of the reaction, but normally a stable activity level is reached within an hour.

The starting materials for catalyst preparation are not critical, but may be any of nitrate, sulfate, oxide, hydroxide, chloride, carbonate, acetate, oxygen acid, ammonium salt of oxygen acid, etc. of the elements.

As Mn source, besides powders of various oxides thereof or molded products which are useful as they are, manganese hydroxide slurries obtained upon treating an aqueous solution of, eg., manganese nitrate, with aqueous ammonia or the like are conveniently used. Any means used for catalyst preparation in general, for example, co-precipitation of a manganese compound with compounds of other additive elements from their aqueous solution, are applicable. As sulfur source, aqueous sulfuric acid or ammonium sulfate may be used, or the whole or a part thereof may be introduced in the form of sulfate(s) of other additive element (s). Similarly, halogen may be introduced as aqueous hydrogen halide or ammonium halide, or in the form of halide(s) of other additive element(s).

Again the use form of refractory inorganic carrier is subject to no critical limitation, which allows versatile selection according to the form of use of the catalyst, such as, besides molded products, powder of oxide or hydroxide, gel or sol.

The starting gas to be subjected to the vapor phase oxidative dehydrogenation reaction according to the present invention may if necessary contain a diluent gas, besides lower alkane(s) and molecular oxygen. As the molecular oxygen, air or pure oxygen is used, normally at a ratio of 0.1–5 mols per mol of alkane. As the diluent gas, an inert gas such as nitrogen, helium or carbon dioxide or steam is conveniently used.

The reaction conditions for carrying out the vapor phase oxidative dehydrogenation of the present invention are subject to no critical limitation. For example, the starting gas as described above is contacted with an oxidative dehydrogenation catalyst of the present invention under such conditions as: at a space velocity of 300–30,000 $hr^{-1}$ at a temperature between 250 and 650° C. While the reaction is normally conducted under atmospheric pressure, a reduced or elevated pressure may be used. The reaction system again is not critical, which may be a fixed bed system, moving bed system or fluidized bed system. It may also be one-pass system or recycling system.

The olefines (alkenes) which are obtained through the vapor phase oxidative dehydrogenation of $C_2$–$C_5$ lower alkanes (alkane oxidative dehydrogenation step) using the catalyst of the present invention can be further oxidized to produce unsaturated aldehydes and unsatuated acids (alkene oxidation step). The unsaturated aldehydes can further be oxidized to produce unsaturated acids (aldehyde oxidation step). Thus formed unsaturated aldehydes and/or unsaturated acids are trapped with an absorption column (absorbing step). As the oxygen source in the present invention, air and/or oxygen produced by such methods as cryogenic method, P.S.A. (pressure swing adsorption) method and the like can be used. According to the present invention, it is possible to form from lower alkanes the corresponding olefins, without side-production of hydrogen. If necessary oxygen and/or steam may be added to the gases to be introduced in each of the above steps, and such additional oxygen and/or steam are supplied by, for example, air, above-described oxygen, water and/or the gas discharged of said absorbing step.

As one specific example of useful catalyst in the alkene oxidation step, those expressed by following general formula (2) may be named:

$$Mo_aBi_bFe_cA_dB_eC_fD_gO_x \quad (2)$$

in which Mo is molybdenum; Bi is bismuth; Fe is iron; A is at least one element selected from the group consisting of cobalt and nickel; B is at least one element selected from the group consisting of alkali metals and thallium; C is at least one element selected from the group consisting of silicon, aluminium, zirconium and titanium; D is at least one element selected from the group consisting of tungsten, phosphorus, tellurium, antimony, tin, cerium, lead, niobium, manganese, arsenic and zinc; and O is oxygen: and the ratio of those elements is, when a=12, b=0.1–10, c=0.1–20, d=2–20, e=0.001–10, f=0–30, g=0–4 and x is a numerical value determined by the state of oxidation of those elements other than oxygen.

Also as one specific example of useful catalyst in the aldehyde oxidation step, those expressed by following general formula (3) may be named:

$$Mo_hV_iW_jE_kF_lG_mH_nO_x \quad (3)$$

in which Mo is molybdenum; V is vanadium; W is tungsten; E is at least one element selected from the group consisting of copper, cobalt, bismuth and iron; F is at least one element selected from the group consisting of antimony and niobium; G is at least one element selected from the group consisting of silicon, aluminium, zirconium and titanium; H is at least one element selected from the group consisting of alkaline earth metals, thallium, phosphorus, tellurium, tin, cerium, lead, manganese and zinc; and O is oxygen: and the ratio of those elements is, when h=12, i=0.1–10, j=0–10, k=0.1–20, l=0–10, m=0–10, n=0–30, and x is a numerical value determined by the state of oxidation of those elements other than oxygen.

EFFECT OF THE INVENTION

The lower alkane oxidative dehydrogenation catalysts according to the present invention excel in the oxidative dehydrogenation ability and enable the production from lower alkanes of corresponding olefins at high yield.

Furthermore, due to their higher activity level than that of known catalyst system, the amount of the catalyst necessary for securing the same level of STY (space time yield) is far less than that of conventional catalysts, such as from 1/3 to 1/10.

Also according to the present invention, unsaturated aldehyde and/or unsaturated acid can be produced from lower alkanes stably at high yield.

EXAMPLES

Hereinafter the invention is explained in further details referring to working examples, in which percentage are by weight, unless otherwise specified, and the conversion, one-pass yield and selectivity are indicated following the definitions below, inclusive of the side products:

$$\text{selectivity (mol \%)} = \frac{\text{(mol number of each of formed compounds)}}{\text{(mol number of reacted alkane)}} \times$$

$$\frac{\text{(carbon number of each of formed compounds)}}{\text{(carbon number of fed alkane)}} \times 100$$

one-pass yield (mol %) =

$$\frac{\text{(mol number of each of formed compounds)}}{\text{(mol number of fed alkane)}} \times$$

$$\frac{\text{(carbon number of each of formed compounds)}}{\text{(carbon number fed alkane)}} \times$$

$$100 = \frac{\text{conversion} \times \text{selectivity}}{100}$$

Example 1

Into a 500-ml beaker, 4.35 g of manganese dioxide powder(MnO$_2$, Kishida Chemical, purity 99.9%) and 200 ml of water were fed and heated under agitation. Further 1.09 g of antimony trioxide powder (Wako Pure Chemical Industry LTD., purity 99.9%) was added to the system which was then heated to about 80° C., and stirred for 2 hours while being maintained at a constant liquid volume. Then the temperature was raised to 90° C. and stirring was continued for about 4 hours allowing concentration by evaporation of water content. The resulting paste was dried for 14 hours at 120° C., pulverized, molded and crushed to uniformize the size to 9–20 mesh. The resulting catalyst had a composition of Mn$_1$Sb$_{0.15}$Ox, 0.6 g of which was charged in an ordinary flow type reactor. The reaction was conduced under the following conditions;

Reaction gas: C$_3$H$_8$/O$_2$/N$_2$=1/1/8 (molar ratio)

Feed rate: 112.5 ml/min.

SV: equivalent to 12,000 hr$^{-1}$ (In the subsequent Examples, indication of SV is omitted. As the catalyst weight was constant, SV underwent fluctuation more or less dependent on its packing density.)

Reaction temperature: 450° C.

The results were as shown in Table 1.

Example 2

The catalyst preparation was conducted in the same manner as in Example 1, except that the amount of the antimony trioxide powder was changed to 1.82 g. The resulting catalyst had a composition of Mn$_1$Sb$_{0.25}$Ox. Using 0.6 g of this catalyst, the reaction was conducted under identical conditions with those of Example 1. The results were as shown in Table 1.

Example 3

The catalyst preparation was conducted in the same manner as in Example 1, except that the antimony trioxide powder was replaced with 0.58 g of 85% phosphoric acid (H$_3$PO$_4$, special grade reagent manufactured by Kanto Chemical) as dissolved in 50 ml of water. The resulting catalyst had a composition of Mn$_1$P$_{0.1}$Ox. Using 0.6 g of this catalyst, the reaction was conducted under identical conditions with those of Example 1, except that the reaction temperature was raised to 490° C. The results were as shown in Table 1.

Example 4

The catalyst preparation was conducted in the same manner as in Example 3, except that the amount of the 85% phosphoric acid was changed to 1.15 g. The resulting catalyst had a composition of $Mn_1P_{0.2}Ox$. Using 0.6 g of this catalyst, the reaction was run under identical conditions with those of Example 3. The results were as shown in Table 1.

Example 5

The catalyst preparation was conducted in the same manner as in Example 1, except that the antimony trioxide powder was replaced with 0.31 g of boric acid ($H_3BO_3$, special grade reagent manufactured by Kanto Chemical) as dissolved in 50 ml of water. The resulting catalyst had a composition of $Mn_1B_{0.1}Ox$. Using 0.6 g of this catalyst, the reaction was run under identical conditions with those of Example 3. The results were as shown in Table 1.

Example 6

The catalyst preparation was conducted in the same manner as in Example 1, except that the antimony trioxide powder was replaced with 0.66 g of ammonium sulfate (special grade reagent manufactured by Kanto Chemical) as dissolved in 50 ml of water. The resulting catalyst had a composition of $Mn_1S_{0.1}Ox$. Using 0.6 g of this catalyst, the reaction was run under identical conditions with those of Example 3. The results were as shown in Table 1.

Example 7

The catalyst preparation was conducted in the same manner as in Example 1, except that the antimony trioxide powder was replaced with 1.62 g of niobium oxalate (a product of C.B.M.M. Co., containing 20.5% of $Nb_2O_5$ upon conversion) as dissolved in 100 ml of water. The resulting catalyst had a composition of $Mn_1Nb_{0.05}Ox$. Using 0.6 g of this catalyst, the reaction was run under identical conditions with those of Example 3. The results were as shown in Table 1.

Example 8

The catalyst preparation was conducted in the same manner as in Example 1, except that the antimony trioxide powder was replaced with 1.16 g of aqueous ammonium meta-tungstate solution, MW-2 (a product of Nippon Inorganic Colour and Chemical Co., LTD., containing 50% of $WO_3$) as diluted with 50 ml of water. The resulting catalyst had a composition of $Mn_1W_{0.05}Ox$. Using 0.6 g of this catalyst, the reaction was run under identical conditions with those of Example 3. The results were as shown in Table 1.

Example 9

The catalyst preparation was conducted in the same manner as in Example 1, except that the antimony trioxide powder was replaced with 0.61 g of rhenium oxide ($Re_2O_7$, Kishida Chemical, purity 99.99%) as dissolved in 50 ml of water. The resulting catalyst had a composition of $Mn_1Re_{0.05}Ox$. Using 0.6 g of this catalyst, the reaction was run under identical conditions with those of Example 3. The results were as shown in Table 1.

Example 10

The catalyst preparation was conducted in the same manner as in Example 1, except that the antimony trioxide powder was replaced with 1.21 g of copper nitrate (Wako Pure Chemical Industry LTD., purity 99.9%) as dissolved in 50 ml of water. The resulting catalyst had a composition of $Mn_1Cu_{0.1}Ox$. Using 0.6 g of this catalyst, the reaction was run under identical conditions with those of Example 3. The results were as shown in Table 1.

Example 11

The catalyst preparation was conducted in the same manner as in Example 1, except that the antimony trioxide powder was replaced with 1.07 g of ammonium chloride (special grade reagent manufactured by Kanto Chemical) as dissolved in 50 ml of water. The resulting catalyst had a composition of $Mn_1Cl_{0.4}Ox$. Using 0.6 g of this catalyst, the reaction was run under identical conditions with those of Example 3. The results were as shown in Table 1.

Example 12

The catalyst preparation was conducted in the same manner as in Example 1, except that 2.00 g of chromium nitrate [$Cr(NO_3)_3 \cdot 9H_2O$, Wako Pure Chemical Industry LTD., purity 99.9%] as dissolved in 50 ml of water was added following the addition of the antimony trioxide powder. The resulting catalyst had a composition of $Mn_1Sb_{0.15}Cr_{0.1}Ox$. Using 0.6 g of this catalyst, the reaction was run under identical conditions with those of Example 1. The results were as shown in Table 1.

Example 13

The catalyst preparation was conducted in the same manner as in Example 1, except that 2.02 g of iron nitrate [$Fe(NO_3)_3 \cdot 9H_2O$, Wako Pure Chemical Industry LTD., special grade reagent] as dissolved in 50 ml of water was added following the addition of the antimony trioxide powder. The resulting catalyst had a composition of $Mn_1Sb_{0.15}Fe_{0.1}Ox$. Using 0.6 g of this catalyst, the reaction was run under identical conditions with those of Example 1. The results were as shown in Table 1.

Example 14

The catalyst preparation was conducted in the same manner as in Example 1, except that 0.42 g of sodium nitrate (Wako Pure Chemical Industry LTD., special grade reagent) as dissolved in 50 ml of water was added following the addition of the antimony trioxide powder. The resulting catalyst had a composition of $Mn_1Sb_{0.15}Na_{0.1}Ox$. Using 0.6 g of this catalyst, the reaction was run under identical conditions with those of Example 1. The results were as shown in Table 1.

Example 15

The catalyst preparation was conducted in the same manner as in Example 1, except that 1.28 g of magnesium nitrate [$Mg(NO_3)_2 \cdot 6H_2O$, Wako Pure Chemical Industry LTD., special grade reagent] as dissolved in 50 ml of water was added following the addition of the antimony trioxide powder. The resulting catalyst had a composition of $Mn_1Sb_{0.15}Mg_{0.1}Ox$. Using 0.6 g of this catalyst, the reaction was run under identical conditions with those of Example 1. The results were as shown in Table 1.

Example 16

The catalyst preparation was conducted in the same manner as in Example 1, except that 2.22 g of cerium nitrate [$Ce(NO_3)_3 \cdot 6H_2O$, Wako Pure Chemical Industry LTD., special grade reagent, purity 98%] as dissolved in 50 ml of water was added following the addition of the antimony trioxide powder. The resulting catalyst had a composition of $Mn_1Sb_{0.15}Ce_{0.1}Ox$. Using 0.6 g of this catalyst, the reaction was run under identical conditions with those of Example 1. The results were as shown in Table 1.

Example 17

The catalyst preparation was conducted in the same manner as in Example 1, except that the antimony trioxide powder was replaced with 1.11 g of chromium sulfate [$Cr_2(SO_4)_3 \cdot 4H_2O$, Kanto Chemical, first grade reagent] as dissolved in 50 ml of water. The resulting catalyst had a composition of $Mn_1S_{0.15}Cr_{0.1}Ox$. Using 0.6 g of this catalyst, the reaction was run under identical conditions with those of Example 3. The results were as shown in Table 1.

Example 18

The catalyst preparation was conducted in the same manner as in Example 1, except that the antimony trioxide powder was replaced with 1.75 g of stannic chloride ($SnCl_4 \cdot 5H_2O$, Wako Pure Chemical Industry LTD., special grade reagent) as dissolved in 50 ml of water. The resulting catalyst had a composition of $Mn_1Cl_{0.4}Sn_{0.1}Ox$. Using 0.6 g of this catalyst, the reaction was run under identical conditions with those of Example 3. The results were as shown in Table 1.

Example 19

The catalyst preparation was conducted in the same manner as in Example 1, except that 1.16 g of aqueous ammonium meta-tungstate solution MW-2 as diluted with 50 ml of water and 2.00 g of chromium nitrate as dissolved in 50 ml of water were added following the addition of the antimony trioxide powder. The resulting catalyst had a composition of $Mn_1Sb_{0.15}W_{0.05}Cr_{0.1}Ox$. Using 0.6 g of this catalyst, the reaction was run under identical conditions with those of Example 1. The results were as shown in Table 1.

Example 20

Using 0.6 g of the catalyst which was used in Example 19, the reaction of Example 19 was repeated except that the reaction temperature was raised to 490° C. The results were as shown in Table 1.

Example 21

The catalyst preparation was conducted in the same manner as in Example 1, except that 1.16 g of aqueous ammonium meta-tungstate solution as diluted with 50 ml of water and 1.11 g of chromium sulfate as dissolved in 50 ml of water were added following the addition of the antimony trioxide powder. The resulting catalyst had a composition of $Mn_1Sb_{0.15}W_{0.05}S_{0.15}Cr_{0.1}Ox$. Using 0.6 g of this catalyst, the reaction was run under identical conditions with those of Example 3. The results were as shown in Table 1.

Example 22

Using 0.6 g of this catalyst which was used in Example 21, the reaction of Example 21 was repeated except that the reaction temperature was raised to 530° C. The results were as shown in Table 1.

Example 23

The catalyst preparation was repeated except that 1.16 g of aqueous ammonium meta-tungstate solution MW-2 as diluted with 50 ml of water, 1.62 g of niobium oxalate as dissolved in 100 ml of water and 2.00 g of chromium nitrate as dissolved in 50 ml of water were added following the addition of the antimony trioxide powder. The resulting catalyst had a composition of $Mn_1Sb_{0.15}W_{0.05}Nb_{0.05}Cr_{0.1}Ox$. Using 0.6 g of this catalyst, the reaction was run under identical conditions with those of Example 3. The results were as shown in Table 1.

Example 24

Using 0.6 g of the same catalyst as used in Example 23, the reaction of Example 23 was repeated except that the reaction temperature was raised to 530° C. The results were as shown in Table 1.

Comparative Example 1

The same manganese dioxide powder as the one used in Example 1 was pulverized, molded and crushed to a uniform size of 9–20 mesh. Using 0.6 g of this catalyst, the reaction was run under identical conditions with those of Example 1. The results were as shown in Table 1.

Comparative Example 2

The reaction of Example 1 was repeated except that 0.6 g the catalyst same to that used in Comparative Example 1 was used and the reaction temperature was raised in 490° C. The results were as shown in Table 1.

Example 25

Using isobutane instead of propane, isobutene was synthesized, assisted by the same catalyst as the one used in Example 19. An ordinary flow type reactor was charged with 0.6 g of the catalyst of 9–20 mesh in size, and through which a reaction gas composed of i-$C_4H_{10}/O_2/N_2$=1/1/8 (molar ratio) was passed at a rate of 112.5 ml/min. The reaction temperature was 450° C. The results were: isobutane conversion 26.5%, isobutene selectivity 27.5%, methacrolein selectivity 0.9% and one-pass yield of isobutene 7.3%.

TABLE 1

| | Reaction Temp. (° C.) | Propane Conversion (%) | Selectivity (%) | | One-Pass Yield (%) |
|---|---|---|---|---|---|
| | | | Propylene | Acrolein | Propylene |
| Example 1 | 450 | 27.3 | 27.1 | 0.3 | 7.4 |
| Example 2 | 450 | 26.9 | 26.7 | 0.7 | 7.2 |
| Example 3 | 490 | 31.2 | 33.4 | 0.3 | 10.4 |
| Example 4 | 490 | 30.9 | 33.7 | 0.3 | 10.4 |
| Example 5 | 490 | 9.7 | 47.3 | 1.4 | 4.6 |
| Example 6 | 490 | 17.9 | 36.3 | 0.4 | 6.5 |
| Example 7 | 490 | 30.3 | 29.6 | 0.2 | 9.0 |
| Example 8 | 490 | 29.7 | 29.4 | 0.2 | 8.7 |
| Example 9 | 490 | 8.4 | 53.8 | 0.2 | 4.5 |
| Example 10 | 490 | 25.3 | 22.2 | 0.1 | 5.6 |
| Example 11 | 490 | 27.1 | 16.1 | 0.1 | 4.4 |
| Example 12 | 450 | 30.0 | 28.0 | 0.5 | 8.4 |
| Example 13 | 450 | 28.1 | 27.8 | 0.6 | 7.8 |
| Example 14 | 450 | 26.5 | 28.7 | 0.3 | 7.6 |
| Example 15 | 450 | 27.4 | 28.1 | 0.3 | 7.7 |
| Example 16 | 450 | 29.2 | 26.7 | 0.4 | 7.8 |
| Example 17 | 490 | 28.8 | 23.8 | 0.1 | 6.9 |
| Example 18 | 490 | 25.5 | 19.8 | 0.1 | 5.0 |
| Example 19 | 450 | 29.8 | 35.2 | 0.1 | 10.5 |
| Example 20 | 490 | 32.8 | 37.9 | 0.3 | 12.4 |
| Example 21 | 490 | 31.6 | 42.9 | 2.0 | 13.6 |
| Example 22 | 530 | 36.5 | 42.6 | 1.8 | 15.5 |
| Example 23 | 490 | 33.6 | 39.9 | 0.7 | 13.5 |
| Example 24 | 530 | 35.5 | 41.7 | 0.8 | 14.8 |
| Comparative Example 1 | 450 | 18.0 | 10.5 | 0 | 1.9 |
| Comparative Example 2 | 490 | 23.7 | 13.4 | 0 | 3.2 |

Example 26

Each independently temperature-controllable single-pipe flow type reactors (A), (B) and (C) were connected in such a manner that gas would flow by the order of (A) to (B) to (C), with the piping so designed that the gas formed in the reactor (C) is introduced into an absorption column to allow absorption of condensed component and introduction of the uncondensed gas flowing out of the absorption column into the reactor A through its gas inlet portion, and the reaction was conducted with the following particulars. The piping also was so connected that fresh air could be introduced into the reactor (B) through its gas inlet portion.

Preparation of Catalyst 9 g of the catalyst as used in Example 21 was packed in the reactor (A), while the reactor (B) was packed with 32 g of a catalyst of the following composition (excepting oxygen) as described in Example 1 of Japanese Patent Publication No. 42241/1972:

$$Mo_{10}Co_4Bi_1Fe_1W_2Si_{1.35}K_{0.05}.$$

The reactor (C) was packed with 52 g of a catalyst of the following composition (excepting oxygen) as described in Example 1 of Japanese KOKAI No. 206504/1996:

$$Mo_{12}V_{6.1}W_1Cu_{2.3}Sb_{1.2}.$$

The flow rates of propane, air and recovered gas from absorption column were so controlled at the gas inlet portion of the reactor (A) as to give the reaction gas composition of 15 vol % $C_3H_8$, 15 vol % $O_2$ and 70 vol % of inert gases comprising nitrogen, carbon oxide, etc. In that occasion, the space velocity to the oxidative dehydrogenation catalyst was 3000 hr$^{-1}$. The product gas from the reactor (A) was fed into the reactor (B) while adding air thereto at such a rate that $O_2/C_3H_6$ ratio therein should become 2.5 at the entrance portion of the reactor (B), and the product gas from the reactor (B) was fed into the reactor (C). The reaction temperatures in the reactors (A), (B) and (C) during the run were 480° C., 325° C. and 250° C., respectively.

Analysis of the product gas from the reactor (C) indicated: $C_3H_8$ conversion, 45.5 mol % and acrylic acid yield, 20.7 mol %.

Example 27

To the reactor assembly used in Example 26, piping was connected to allow introduction of fresh air and steam into the gas inlet portion of the reactor (C), and the reaction was carried out with the particulars as follows.

The flow rates of propane and gaseous oxygen were so controlled at the gas inlet portion of the reactor (A) as to give the reaction gas composition of 30 vol % $C_3H_8$, 30 vol % $O_2$ and 40 vol % of inert gases comprising nitrogen, carbon oxide, etc. The space velocity to the oxidative dehydrogenation catalyst in that occasion was 4,000 hr$^{-1}$. The product gas from the reactor (A) was fed into the reactor (B) while adding air thereto at such a rate that the $O_2/C_3H_6$ ratio therein should become 1.5 at the gas inlet portion of the reactor (B). The product gas from the reactor (B) was fed into the reactor (C), while adding air and steam thereto at such rates that the $O_2$/acrolein ratio and steam concentration therein should become 1.3 and 35 vol %, respectively, at the gas inlet portion of the reactor (C). Other conditions were identical with those of Example 26.

Analysis of the product gas from the reactor (C) indicated: $C_3H_8$ conversion, 44.1 mol % and acrylic acid yield, 20.1 mol %.

What is claimed is:

1. In a process for producing an olefin by the vapor phase oxidative dehydrogenation of alkane having from 2 to 5 carbon atoms in the presence of molecular oxygen, the improvement comprising, carrying out the vapor phase oxidative dehydrogenation in the presence of an oxidative dehydrogenation catalyst comprising a multimetal mixed oxide having the formula $$Mn_\alpha E^1_\beta E^2_\gamma O_x \qquad (1)$$

where Mn denotes manganese;

O denotes oxygen;

$E^1$ represents one or more metal elements selected from the group consisting of phosphorus, arsenic, antimony, boron, sulfur, selenium, tellurium, fluorine, chlorine, bromine, iodine, niobium, tantalum, tungsten, rhenium and copper;

$E^2$ represents one or more metal elements selected from the group consisting of chromium, iron, cobalt, nickel, silver, gold, zinc, thallium, tin, lead, bismuth, lithium, sodium, potassium, rubidium, cesium, magnesium, calcium, strontium, barium, yttrium, lanthanum, cerium, neodymium, and samarium; and, $\alpha$, $\beta$, $\gamma$ and x denote atomic numbers of Mn, $E^1$, $E^2$, and oxygen, respectively, and, when $\alpha=1$, $\beta=0.01–10$, $\gamma=0–5$, and x has a numerical value determined by the state of oxidation of the elements other than oxygen.

2. The process according to claim 1, wherein, in the oxidative dehydrogenation catalyst of formula (1), when $\alpha=1$, $\beta=0.02–2$ and $\gamma=0–1$.

3. The process according to claim 1, wherein the oxidative dehydrogenation catalyst of formula (1) is one which is dried and fired at temperatures not higher than 300° C.

4. The process according to claim 1, wherein the oxidative dehydrogenation catalyst is supported on a refractory inorganic carrier.

5. The process according to claim 1, wherein the oxidative dehydrogenation of said alkane is carried out at a space velocity of from 300 to 30,000 hr$^{-1}$, and at a temperature of from 250 to 650°C.

6. The process according to claim 1, wherein the oxidative dehydrogenation catalyst is selected from the group consisting of $Mn_1Sb_{0.15}O_x$, $Mn_1Sb_{0.25}O_x$, $Mn_1B_{0.1}O_x$, $Mn_1S_{0.1}O_x$, $Mn_1Nb_{0.05}O_x$, $Mn_1W_{0.05}O_x$, $Mn_1Re_{0.05}O_x$, $Mn_1Cu_{0.1}O_x$, $Mn_1Cl_{0.4}O_x$, $Mn_1Sb_{0.15}Cr_{0.1}O_x$, $Mn_1Sb_{0.15}Na_{0.1}O_x$, $Mn_1Sb_{0.15}Mg_{0.1}O_x$, $Mn_1Sb_{0.15}Ce_{0.1}O_x$, $Mn_1S_{0.15}Cr_{0.1}O_x$, $Mn_1Cl_{0.4}Sn_{0.1}O_x$, $Mn_1Sb_{0.15}W_{0.05}Cr_{0.1}O_x$, $Mn_1Sb_{0.15}W_{0.05}S_{0.15}Cr_{0.1}O_x$, and $Mn_1Sb_{0.15}W_{0.05}Nb_{0.05}Cr_{0.1}O_x$.

* * * * *